United States Patent
Kondo et al.

(10) Patent No.: US 9,920,272 B2
(45) Date of Patent: Mar. 20, 2018

(54) IONIC LIQUID, LUBRICANT, AND MAGNETIC RECORDING MEDIUM

(71) Applicant: DEXERIALS CORPORATION, Shinagawa-ku, Tokyo (JP)

(72) Inventors: Hirofumi Kondo, Tokyo (JP); Kouki Hatsuda, Tokyo (JP); Makiya Ito, Tokyo (JP); Nobuo Tano, Tokyo (JP); Kyungsung Yun, Tokyo (JP); Masayoshi Watanabe, Kanagawa (JP)

(73) Assignee: DEXERIALS CORPORATION, Shinagawa-Ku, Tokyo (JP)

( * ) Notice: Subject to any disclaimer, the term of this patent is extended or adjusted under 35 U.S.C. 154(b) by 0 days.

(21) Appl. No.: 15/319,697

(22) PCT Filed: May 19, 2015

(86) PCT No.: PCT/JP2015/064248
§ 371 (c)(1),
(2) Date: Dec. 16, 2016

(87) PCT Pub. No.: WO2015/194294
PCT Pub. Date: Dec. 23, 2015

(65) Prior Publication Data
US 2017/0137736 A1 May 18, 2017

(30) Foreign Application Priority Data
Jun. 19, 2014 (JP) .................................. 2014-126337

(51) Int. Cl.
*C10M 105/72* (2006.01)
*C07D 233/58* (2006.01)
(Continued)

(52) U.S. Cl.
CPC ......... *C10M 105/72* (2013.01); *C07C 309/06* (2013.01); *C07D 233/58* (2013.01);
(Continued)

(58) Field of Classification Search
CPC .............. C10M 105/70; C10M 105/72; C10M 159/12; C10M 2215/221; C10M 2219/044;
(Continued)

(56) References Cited

U.S. PATENT DOCUMENTS

2005/0282044 A1* 12/2005 Kobayashi .............. C07C 69/63
428/843.4
2007/0066822 A1   3/2007 Harmer et al.
(Continued)

FOREIGN PATENT DOCUMENTS

JP   2581090 B2   2/1997
JP   2629725 B2   7/1997
(Continued)

OTHER PUBLICATIONS

English-language machine translation of JP 2005-048139 A.*
(Continued)

*Primary Examiner* — James Goloboy
(74) *Attorney, Agent, or Firm* — Buchanan, Ingersoll & Rooney PC

(57) ABSTRACT

A lubricant including an ionic liquid, which includes a conjugate acid ($B^+$) and a conjugate base ($X^-$), and is protic, wherein the ionic liquid is represented by the following general formula (1):

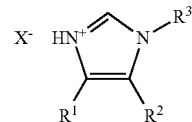

General formula (1)

where $R^1$ and $R^2$ each represent a hydrogen atom or $R^1$ and $R^2$ form a benzene ring together with carbon atoms to which $R^1$ and $R^2$ are bonded, and $R^3$ represents a straight-chain hydrocarbon group having 10 or more carbon atoms in the general formula (1).

5 Claims, 3 Drawing Sheets

(51) Int. Cl.
| | |
|---|---|
| *C07D 285/06* | (2006.01) |
| *G11B 5/725* | (2006.01) |
| *C10M 159/12* | (2006.01) |
| *C10M 105/70* | (2006.01) |
| *C07C 309/06* | (2006.01) |
| *C07D 285/16* | (2006.01) |

(52) U.S. Cl.
CPC ......... *C07D 285/16* (2013.01); *C10M 105/70* (2013.01); *C10M 159/12* (2013.01); *G11B 5/725* (2013.01); *C10M 2215/221* (2013.01); *C10M 2219/044* (2013.01); *C10N 2220/04* (2013.01); *C10N 2240/204* (2013.01)

(58) Field of Classification Search
CPC ......... C10N 2220/04; C10N 2240/204; C07D 233/58; C07D 285/16; C07C 309/06; G11B 5/725
See application file for complete search history.

(56) References Cited

U.S. PATENT DOCUMENTS

| | | | |
|---|---|---|---|
| 2007/0112294 A1* | 5/2007 | Akiyama | A61N 1/30 604/20 |
| 2009/0069204 A1* | 3/2009 | Kamimura | C10M 169/04 508/100 |
| 2009/0170734 A1 | 7/2009 | Schwab et al. | |

FOREIGN PATENT DOCUMENTS

| | | |
|---|---|---|
| JP | 2005048139 A * | 2/2005 |
| JP | 2009-511434 A | 3/2009 |
| JP | 2010-168544 A | 8/2010 |
| JP | 2011-016791 A | 1/2011 |
| JP | 2011-026296 A | 2/2011 |
| WO | WO 2006/077082 A1 | 7/2006 |

OTHER PUBLICATIONS

International Search Report (PCT/ISA/210) dated Aug. 11, 2015, by the Japanese Patent Office as the International Searching Authority for International Application No. PCT/JP2015/064248.
Written Opinion (PCT/ISA/237) dated Aug. 11, 2015, by the Japanese Patent Office as the International Searching Authority for International Application No. PCT/JP2015/064248.
Chen, Yunxia et al., "Tribological performance of an ionic liquid as a lubricant for steel/aluminium contacts", J. Synthetic Lubricant, 20-3, Oct. 2003, pp. 217-225.
Jimenez, A. E. et al., 1-N-alkyl-3-methylimidazolium ionic liquids as neat lubricants and lubricant additives in steel-aluminum contacts:, Wear, 260, 2006, pp. 766-782.
Kondo, Hirofumi et al., "Comparison of an Amide and Amine Salt as Friction Modifiers for a Magnetic Thin Film Medium", Tribology Transactions, vol. 37, No. 1, 1994, pp. 99-104, ISSN; 0569-8197.
Kondo, Hirofumi et al., "Novel Lubricants for Magnetic Thin Film Media", Journal of the Magnetic Society of Japan, 1989, vol. 13, Suppl. No. SI, pp. 213-218.
Kondo, Hirofumi et al., "Frictional Properties of Novel Lubricants for Magnetic Thin Film Media", IEEE Transactions on Magnetics, Sep. 1990, vol. 26, No. 5, pp. 2691-2693, ISSN: 0018-9464.
Kondo, Hirofumi et al., "New ionic liquid lubricants for magnetic thin film media", IEEE Transactions Magnetics, Jul. 2013, vol. 49, No. 7, pp. 3756-3759.
Liu, Weimin et al., "Tribological performance of room-temperature ionic liquids as lubricant", Tribology Letters, Aug. 2002, vol. 13, No. 2, pp. 81-85.
Merrigan, Travis L. et al., "New fluorous ionic liquids function as surfactants in conventional room-temperature ionic liquids", Chem. Comm., Oct. 21, 2000, No. 20, pp. 2051-2052.
Stiemke, Frank et al., "Ionic Liquids: High Performance Additives for Lubricants", STLE Annual Meeting, Detroit, May 5-9, 2013, 35 pages.
Wasserscheid, Peter et al., "Hydrogensulfate and tetrakis(hydrogensulfato)borate ionic liquids: synthesis and catalytic application in highly Bronsted-acidic systems for Friedel-Crafts alkylation", Green Chemistry, 2002, vol. 4, pp. 134-138.
Weng, LiJun et al., "Effect of tetraalkylphosphonium based ionic liquids as lubricants on the tribological performance of a steel-on-steel system", Tribology Letters, Apr. 2007, vol. 26, No. 1, pp. 11-17.
Ye, Chengfeng et al. "Room-temperature ionic liquids: a novel versatile lubricant", Chem. Commun., 2001, pp. 2244-2245.
Yu, Guiqin et al., "Preparation of functional ionic liquids and tribological investigation of their ultra-thin films", Wear, 2006, vol. 260, pp. 1076-1080.
Zhang, Qinghua et al., "Physicochemical properties of nitrile-functionalized ionic liquids", J. Phys. Chem. B, 2007, vol. 111, pp. 2864-2872.
Rollins et al.: "Kinetics and Thermodynamics of Hydrogen Oxidation and Oxygen Reduction in Hydrophobic Room-Temperature Ionic Liquids," Journal of the Electrochemical Society, 2009, 156(8), pp. b943-b954 (12 Pages).
Mukai et al.: "Self-assembled N-Alkylimidazolium Perfluorooctanesulfonates," Chemistry Letters, 2005, vol. 34, No. 3, pp. 442-443 (2 pages).
Pernak et al.: "New Ionic Liquids with Organic Anions," Polish Journal of Chemistry, 2003, vol. 77, No. 8, pp. 975-984 (10 pages).
Li et al.: "Ionic liquid crystalline phases in 3-hexadecylimidazolium bromide and binary mixtures with 1-decanol," Journal of Colloid and Interface Science, 2011, 359(2), pp. 474-480 (7 pages).
Notification of Reasons for Refusal issued by the Japanese Patent Office in corresponding Japanese Patent Application No. 2014-126337 dated Dec. 19, 2017 (8 pages including partial English translation).

\* cited by examiner

IONIC LIQUID, LUBRICANT, AND MAGNETIC RECORDING MEDIUM

TECHNICAL FIELD

The present invention relates to a protic ionic liquid, a lubricant containing the ionic liquid, and a magnetic recording medium using the lubricant.

BACKGROUND ART

Conventionally, in a thin film magnetic recording medium, a lubricant is applied onto a surface of a magnetic layer for the purpose of reducing frictions between a magnetic head and the surface of the magnetic recording medium, or reducing abrasion. In order to avoid adhesion, such as sticktion, an actual film thickness of the lubricant is of a molecular order. Accordingly, it is not exaggeration to say that the most important thing for a thin film magnetic recording medium is to select a lubricant having excellent abrasion resistance in any environment.

During a life of a magnetic recording medium, it is important that a lubricant is present on a surface of the medium without causing desorption, spin-off, and chemical deteriorations. Making the lubricant present on a surface of a medium is more difficult, as the surface of the thin film magnetic recording medium is smoother. This is because the thin film magnetic recording medium does not have an ability of replenishing a lubricant as with a coating—type magnetic recording medium.

In the case where an adhesion force between a lubricant and a protective film disposed at a surface of a magnetic layer is weak, moreover, a film thickness of the lubricant is reduced during heating or sliding hence accelerating abrasion. Therefore, a large amount of the lubricant is required. The large amount of the lubricant is the mobile lubricant, and therefore a function of replenishing the lost lubricant can be provided. However, an excessive amount of the lubricant makes the film thickness of the lubricant larger than the surface roughness. Therefore, a problem associated with adhesion arises, and in a crucial case, sticktion arises to cause driving failures. These problems associated with frictions have not been sufficiently solved by conventional perfluoropolyether (PFPE)-based lubricants.

Particularly for a thin film magnetic recording medium having high surface smoothness, a novel lubricant is designed at a molecular level, and synthesized to solve the above-described trade-off. Moreover, there are a number of reports regarding lubricity of PFPE. As described, lubricants are very important in magnetic recording media.

Chemical structures of typical PFPE-based lubricants are depicted in Table 1.

TABLE 1

| Fomblin-based lubricants | |
|---|---|
| | $X-CF_2(OCF_2CF_2)_n(OCF_2)_mOCF_2-X (0.5 < n/m < 1)$ |
| Z | $X = -OCF_3$ |
| Z-DOL | $X = -CH_2OH$ |
| Z-DIAC | $X = -COOH$ |
| Z-Tetraol | $X = -CH_2\ OCH_2CHCH_2OH$<br>　　　　　　　　　　OH |
| AM2001 | $X = -CH_2OCH_2-$ 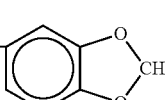 |

| Other lubricants | |
|---|---|
| A20H | $HOCH_2CF_2(OCF_2CF_2)_n(OCF_2)_mOCF_2CH_2O-$ 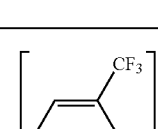 |
| Mono | $F-(CF_2CF_2CF_2O)_1-CF_2CF_2CH_2-N(C_3H_7)_2$ |

Z-DOL in Table 1 is one of lubricants typically used for thin-film magnetic recording media. Moreover, Z-Tetraol (ZTMD) is a lubricant, in which a functional hydroxyl group is further introduced into a main chain of PFPE, and it has been reported that use of Z-Tetraol enhances reliability of a drive while reducing a space at an interface between a head and a medium. It has been reported that A20H suppresses decomposition of the PFPE main chain with Lewis acid or Lewis base, and improves tribological properties. On the other hand, it has been reported that Mono has a different polymer main chain and different polar groups to those of the PFPE, and the polymer main chain and polar groups of Mono are respectively poly-n-propyloxy, and amine, and Mono reduces adhesion interactions at near contact.

However, a typical solid lubricant, which has a high melting point and is considered thermally stable, disturbs an electromagnetic conversion process that is extremely highly sensitive, and moreover, an abrasion powder scraped by a head is generated on a running track. Therefore, abrasion properties are deteriorated. As described above, the liquid lubricant has mobility that enables to move the adjacent lubricant layer to replenish the lubricant removed due to abrasion by the head. However, the lubricant is span-off from a surface of the disk especially at a high temperature during driving of the disk, because of the mobility of the lubricant, and thus the lubricant is reduced. As a result, a protection function is lost. Accordingly, a lubricant having a high viscosity and low volatility is suitably used, and use of such a lubricant enables to prolong a service life of a disk drive with suppressing an evaporation rate.

Considering the above-described lubricating systems, requirements for a low-friction and low-abrasion lubricant used for thin film magnetic recording media are as follows.
(1) Low volatility.
(2) Low surface tension for a surface filling function.
(3) Interaction between terminal polar groups and a surface of a disk.
(4) High thermal and oxidization stability in order to avoid decomposition or reduction over a service period.
(5) Chemically inactive with metals, glass, and polymers, and no abrasion powder generated from a head or a guide.
(6) No toxicity and no flammability.
(7) Excellent boundary lubricating properties.
(8) Soluble with organic solvents.

Recently, an ionic liquid has been attracted attentions as one of solvents for synthesis of organic or inorganic materials and being friendly to the environments in the fields of electricity storage materials, a separation technology, and a catalyst technology. The ionic liquid is roughly classified as a molten salt having a low melting point. The ionic liquid is typically a molten salt having a melting point of 100° C. or lower, among the above-mentioned molten salts. The important properties of the ionic liquid used as a lubricant are low volatility, inflammability, thermal stability, and an excellent dissolving performance. Accordingly, because of the characteristics of the ionic liquid, the ionic liquid is expected to be applicable as a novel lubricant used in an extreme environment, such as in vacuum, and high temperature. Moreover, known is a technique where a controllability of a transistor is enhanced 100 times a controllability of a conventional transistor by using an ionic liquid in a gate of a single self-assembled quantum dot transistor. In this technique, the ionic liquid forms an electric double layer, which functions as an insulating film of about 1 nm, to thereby obtain a large capacitance.

Among others, there have been a considerable number of reports on an imidazole-based aprotic ionic liquid. For example, abrasion and wear of a surface of a metal or ceramic may be reduced by using a certain ionic liquid compared to a conventional hydrocarbon-based lubricant. For example, there is a report that, in the case where an imidazole cation-based ionic liquid is synthesized by substituting with a fluoroalkyl group, and tetrafluoroboric acid salt or hexafluorophosphoric acid salt of alkyl imidazolium is used for steel, aluminium, copper, single crystal $SiO_2$, silicon, or sialon ceramics (Si—Al—O—N), tribological properties more excellent than those of cyclic phosphazene (X-1P) or PFPE are exhibited. Moreover, there is a report that an ammonium-based ionic liquid reduces frictions more than a base oil in the region of elastohydrodynamic to boundary lubrication.

Also, there has been proposed a synthetic lubricant obtained by adding an imidazole-based compound having a long-chain alkyl group to an aprotic ionic liquid containing bis(fluorosulfonyl)imideimidazolium as a main component (see PTL 1). In this proposed technique, observation of abrasion traces generated on a test steel plate after completion of an abrasion test confirms that the proposed synthetic lubricant provides a lowered coefficient of friction and improved abrasion compared to a system free of the imidazole-based compound having a long-chain alkyl group.

Also, most of the ionic liquid-based lubricants having imidazolium have been reported to be based on tetrafluoroborate $[BF_4]^-$ which is an anion based on boron (see NPL 1 to NPL 5).

Also, an aprotic ionic liquid containing $BF_4^-$ has been reported to have significantly favorable tribological performances in steel-steel contacts and steel-aluminum contacts (see NPL 6).

These reports suggest that $BF_4^-$ has excellent tribological performances, but unfortunately its detailed mechanism is not described.

Also, there has been proposed a lubricant exhibiting excellent tribological performances at 20° C. and 100° C. in steel-steel contacts compared to conventional high-temperature lubricants such as X-IP and perfluoropolyether (PFPE) (see NPL 7).

However, $BF_4^-$ is hydrophilic and has high sensitivity to moisture, and thus is not desired in tribology and other industrial applications. These kinds of anions are very sensitive to moisture and can be hydrolyzed to form hydrogen fluoride. These kinds of products cause erosion via various tribochemical reactions, which may cause damages on the substrates in machine systems. Therefore, it is necessary to increase hydrophobicity of anions to decrease their reactivity to moisture and provide a lubricant having tribological properties excellent even in various environments.

The following are proposed as imidazolium-based novel ionic liquids containing an anion fluoride, which are useful as ionic liquids.

Specifically, examples include an imidazole derivative ionic liquid having a fluorine-based end (see NPL 8) and an imidazole derivative ionic liquid having bis(trifluoromethanesulfonate)amide anion (see NPL 9).

There is also proposed a partially-fluorinated sulfonate-based aprotic ionic liquid having an octadecyl group at position 1 (see PTL 2). However, in this proposed technique, actual application properties are not described.

Moreover, effects of the ionic liquid as an additive for a base oil have been studied, and a chemical or tribochemical reaction of the ionic liquid has been researched to understand lubricating systems. However, there are almost no application examples of the ionic liquid to magnetic recording media.

Meanwhile, a protic ionic liquid (PIL) is a collective name of a compound formed by a chemical reaction between Bronsted acid and an equivalent amount of Bronsted base. It has been reported that perfluorooctanoic acid alkyl ammonium salt is PIL, and has a significant effect of reducing frictions of a magnetic recording medium compared with the above-mentioned Z-DOL (see PTL 3 and PTL 4, and NPL 10 to NPL 12).

Moreover, protonic ionic liquids are synthesized more easily than aprotic ionic liquids. For example, protonic ionic liquids have no need to synthesize a quaternary salt of nitrogen and can be synthesized simply by mixing equimolar amounts of an acid and a base. As a result, for example, possible molecular designs for, for example, increasing thermal stability become very variable.

Reported is a lubricant for a magnetic recording medium where thermal stability of the lubricant is enhanced by making a difference (ΔpKa) between pKa of acid and pKa of base large using sulfonic acid ammonium salt (see NPL 13). In this report, it has been confirmed that a mechanism of thermal stability of the lubricant is different depending on a value of ΔpKa, and a weight loss is endothermic and the weight loss occurs due to evaporation in the case where a value of ΔpKa as measured by DG/DTA is small, whereas a weight loss is exothermic and the weight loss is dominantly caused by thermal decomposition in the case where a value of ΔpKa is large.

Meanwhile, hard disks have been developed aiming the surface recording density of from 1 Tb/in² to 2.5 Tb/in². Currently, developments of techniques for large capacities of recording media have been actively performed with reduction in a size of magnetic particles as a premise. As a technique for a large capacity of a recording medium, there are techniques, such as reduction in an effective flying height, and introduction of Single Write (BMP).

As a recording technique of the next generation, moreover, there is "heat assisted magnetic recording." FIG. 3 illustrates a schematic view of heat-assisted magnetic recording. In FIG. 3, reference numeral 1 is laser light, reference numeral 2 is near-field light, reference numeral 3 is a recording head (PMR element), and reference numeral 4 is a reproducing head (TMR element). Examples of a problem of this technique include a deterioration of durability due to evaporation or decomposition of a lubricant present on a surface of a magnetic layer, because a recording area is heated with laser at the time of recording and reproducing. In heat-assisted magnetic recording, a recording medium may be exposed to a high temperature, such as 400° C. or higher, even though it is for a short period. Therefore, thermal stability of a lubricant is concerned, if the lubricant is a typically used lubricant Z-DOL for thin film magnetic recording media, or a carboxylic acid ammonium salt-based lubricant.

CITATION LIST

Patent Literature

PTL 1: Japanese Patent Application Laid-Open (JP-A) No. 2010-168544
PTL 2: JP-A No. 2009-511434
PTL 3: Japanese Patent (JP-B) No. 2581090
PTL 4: JP-B No. 2629725

Non Patent Literature

NPL 1: Ye, C., Liu, W., Chen, Y., Yu, L.: Room-temperature ionic liquids: a novel versatile lubricant. Chem. Commun. 2244-2245 (2001).
NPL 2: Liu, W., Ye, C., Gong, Q., Wang, H., Wang, P.: Tribological performance of room-temperature ionic liquids as lubricant. Tribol. Lett. 13 (2002) 81-85.
NPL 3: Chen, Y. X., Ye, C. F., Wang, H. Z., Liu, W. M.: Tribological performance of an ionic liquid as a lubricant for steel/aluminium contacts. J. Synth. Lubri. 20 (2003) 217-225.
NPL 4: Jimenez, A. E., Bermudez, M. D., Iglesias, P., Carrion, F. J., Martinez-Nicolas, G.: 1-N-alkyl-3-methylimidazolium ionic liquids as neat lubricants and lubricant components in steel aluminum contacts. Wear 260 (2006) 766-782.
NPL 5: Yu, G., Zhou, F., Liu, W., Liang, Y., Yan, S.: Preparation of functional ionic liquids and tribological investigation of their ultra-thin films. Wear 260 (2006) 1076-1080.
NPL 6: Q. Zhang, Z. Li, J. Zhang, S. Zhang, L. Zhu, J. Yang, X. Zhang, Y. J. Deng. Physicochemical properties of nitrile-functionalized ionic liquids. J. Phys. Chem. B, 2007, 111, 2864-2872
NPL 7: L. Wenga, X. Liu, Y. Liang, Q. Xue. Effect of tetraalkylphosphonium based ionic liquids as lubricants on the tribological performance of a steel-on-steel system. Tribol. Lett. 26 (2007) 11-17.
NPL 8: Merrigan et al., Chem. Comm. (2000) 2051-2052
NPL 9: Wasserscheid et al., Green Chemistry (2002) 4: 134-138
NPL 10: Kondo, H., Seto, J., Haga. S., Ozawa, K., (1989) Novel Lubricants for Magnetic Thin Film Media, Magnetic Soc. Japan, Vol. 13, Suppl. No. S1, pp. 213-218
NPL 11: Kondo, H., Seki, A., Watanabe, H., & Seto, J., (1990). Frictional Properties of Novel Lubricants for Magnetic Thin Film Media, IEEE Trans. Magn. Vol. 26, No. 5, (September 1990), pp. 2691-2693, ISSN: 0018-9464
NPL 12: Kondo, H., Seki, A., & Kita, A., (1994a). Comparison of an Amide and Amine Salt as Friction Modifiers for a Magnetic Thin Film Medium. Tribology Trans. Vol. 37, No. 1, (January 1994), pp. 99-105, ISSN: 0569-8197
NPL 13: Hirofumi Kondo, Makiya Ito, Kouki Hatsuda, Kyungsung Yun, Masayoshi Watanabe, New ionic liquid lubricants for magnetic thin film media IEEE Trans. Magn., 2013, Vol. 49, issue 7, pp. 3756-3759

SUMMARY OF INVENTION

Technical Problem

The present invention aims to solve the above-described various problems in the conventional art, and achieve the following object. Specifically, the present invention has an object to provide an ionic liquid having excellent lubricity even at a high temperature, a lubricant having excellent lubricity even at a high temperature, and a magnetic recording medium having excellent practical properties even at a high temperature.

Solution to Problem

Means for solving the above-described problems are as follows:
<1> A lubricant including:
an ionic liquid, which includes a conjugate acid (B⁺) and a conjugate base (X⁻), and is protic,
wherein the ionic liquid is represented by the following general formula (1):

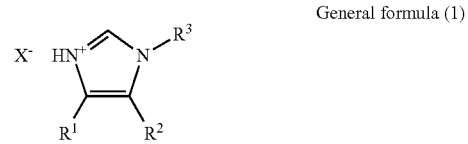

General formula (1)

where $R^1$ and $R^2$ each represent a hydrogen atom or $R^1$ and $R^2$ form a benzene ring together with carbon atoms to which $R^1$ and $R^2$ are bonded, and $R^3$ represents a straight-chain hydrocarbon group having 10 or more carbon atoms in the general formula (1).
<2> The lubricant according to <1>,
wherein the conjugate base is represented by any one of the following general formulae (2) to (4):

General formula (2)

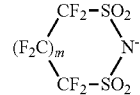

General formula (3)

-continued

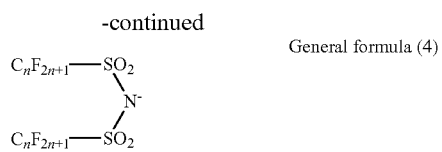
General formula (4)

where n is an integer of 0 to 20 in the general formula (2), m is an integer of 0 to 2 in the general formula (3), and n is an integer of 0 to 10 in the general formula (4).
<3> A magnetic recording medium including:
a non-magnetic support;
a magnetic layer on the non-magnetic support; and
the lubricant according to <1> or <2> on the magnetic layer.
<4> An ionic liquid including:
a conjugate acid ($B^+$); and
a conjugate base ($X^-$),
wherein the ionic liquid is represented by the following general formula (1) and is protic:

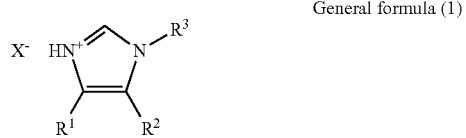
General formula (1)

where $R^1$ and $R^2$ each represent a hydrogen atom or $R^1$ and $R^2$ form a benzene ring together with carbon atoms to which $R^1$ and $R^2$ are bonded, and $R^3$ represents a straight-chain hydrocarbon group having 10 or more carbon atoms in the general formula (1).
<5> The ionic liquid according to <4>,
wherein the conjugate base is represented by any one of the following general formulae (2) to (4):

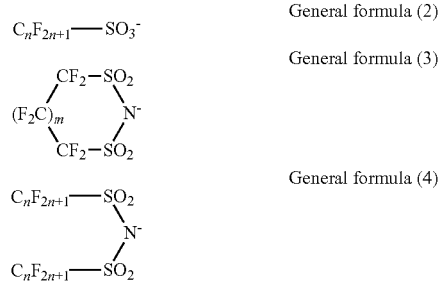
General formula (2)

General formula (3)

General formula (4)

where n is an integer of 0 to 20 in the general formula (2), m is an integer of 0 to 2 in the general formula (3), and n is an integer of 0 to 10 in the general formula (4).

Advantageous Effects of the Invention

The present invention can solve the above-described various problems in the conventional art, and can provide an ionic liquid having excellent lubricity even at a high temperature, a lubricant having excellent lubricity even at a high temperature, and a magnetic recording medium having excellent practical properties even at a high temperature.

Figure 1:
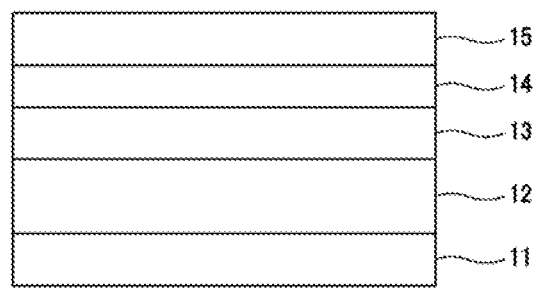
FIG. 1 is a cross-sectional view illustrating one example of a hard disk according to one embodiment of the present invention.

DESCRIPTION OF EMBODIMENTS (Lubricant and Ionic Liquid)

A lubricant of the present invention includes an ionic liquid of the present invention, and may further include other components according to the necessity.

The ionic liquid includes a conjugate acid ($B^+$) and a conjugate base ($X^-$).

The ionic liquid is protic.

The ionic liquid is represented by the following general formula (1):

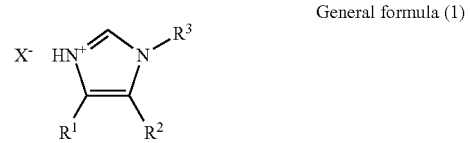
General formula (1)

where $R^1$ and $R^2$ each represent a hydrogen atom or $R^1$ and $R^2$ form a benzene ring together with carbon atoms to which $R^1$ and $R^2$ are bonded, and $R^3$ represents a straight-chain hydrocarbon group having 10 or more carbon atoms in the general formula (1).

The ionic liquid being protic means that the ionic liquid has a proton donor ability, and means, for example, a state where a hydrogen atom is bonded to a cationic atom of the conjugate acid ($B^+$).

<Conjugate Acid>

The conjugate acid is represented by the following general formula (6):

General formula (6)

where $R^1$ and $R^2$ each represent a hydrogen atom or $R^1$ and $R^2$ form a benzene ring together with carbon atoms to which $R^1$ and $R^2$ are bonded, and $R^3$ represents a straight-chain hydrocarbon group having 10 or more carbon atoms in the general formula (6).

Note that, the conjugate acids in the general formulae (1) and (6) may have other resonance structures (canonical structures). Specifically, the conjugate acids can have resonance structures (canonical structures), in which the nitrogen atom to which $R^3$ is bonded is positively charged, and a hydrogen atom is bonded to the nitrogen atom. In the present invention, a conjugate acid having such a resonance structure (a canonical structure) is also included in the conjugate acid represented by the general formula (1) and the conjugate acid represented by the general formula (6).

The upper limit of the number of carbon atoms of the straight-chain hydrocarbon group having 10 or more carbon atoms in the $R^3$ is not particularly limited and may be appropriately selected depending on the intended purpose. The number of carbon atoms is preferably 30 or less, more preferably 25 or less, and particularly preferably 20 or less in view of readily availability of raw materials. Since the hydrocarbon group has a long chain, a coefficient of friction can be reduced, and lubricity is therefore improved.

As long as the hydrocarbon group is in the form of a straight chain, the hydrocarbon group may be a saturated hydrocarbon group, or an unsaturated hydrocarbon group containing double bonds at a part, or an unsaturated branched hydrocarbon group partially containing a branched structure. Among them, the hydrocarbon group is preferably an alkyl group, which is a saturated hydrocarbon group, in view of abrasion resistance. Moreover, the hydrocarbon group is also preferably a straight-chain hydrocarbon group that does not have any branch even partially.

The conjugate acid is preferably a conjugate acid represented by the following general formula (6-1) or (6-2):

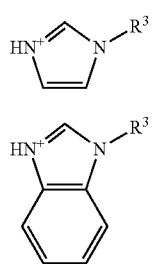

General formula (6-1)

General formula (6-2)

where $R^3$ represents a straight-chain hydrocarbon group having 10 or more carbon atoms in the general formulae (6-1) and (6-2).

<Conjugate Base ($X^-$)>

The conjugate base ($X^-$) is not particularly limited and may be appropriately selected depending on the intended purpose. It is preferably a conjugate base of sulfonic acid, a conjugate base of sulfonimide, and a conjugate base of trisulfonylmethide.

Examples of the conjugate base of sulfonic acid include conjugate bases represented by the following general formula (2).

Examples of the conjugate base of sulfonamide include conjugate bases represented by the following general formula (3) and conjugate bases represented by the following general formula (4).

Examples of the conjugate base of trisulfonylmethide include conjugate bases represented by the following general formula (5).

Among them, conjugate bases represented by the following general formulae (2) to (4) are particularly preferable.

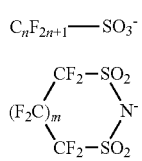

General formula (2)

General formula (3)

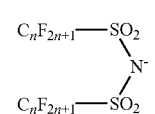

General formula (4)

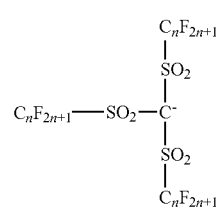

General formula (5)

In the general formula (2), n is an integer of 0 to 20. In the general formula (3), m is an integer of 0 to 2. In the general formula (4), n is an integer of 0 to 10. In the general formula (5), n is an integer of 0 to 6.

n in the general formula (2) is preferably an integer of 1 to 10.

m in the general formula (3) is preferably 1 or 2.

n in the general formula (4) is preferably an integer of 0 to 6.

n in the general formula (5) is preferably an integer of 0 to 4.

A synthesis method of the ionic liquid is not particularly limited and may be appropriately selected depending on the intended purpose. Examples thereof include a synthesis method of mixing equimolar amounts of an alkali metal salt of sulfonic acid or sulfoimide corresponding to the conjugate base and a nitric acid salt of a base corresponding to the conjugate acid, and a synthesis method of mixing equimolar amounts of sulfonic acid corresponding to the conjugate base and a base corresponding to the conjugate acid.

The protic ionic liquids are synthesized more easily than aprotic ionic liquids because the protic ionic liquids have no need to make a nitrogen atom quaternized and can be obtained simply via an acid-base reaction. However, in order to reduce its dissociation to increase thermal stability, it is necessary to use an acid having a low pKa. Specifically, the acid preferably used has a pKa in dichloroethane of less than −10. Examples thereof include acids represented by the following general formula (2-1), acids represented by the following general formula (3-1), and acids represented by the following general formula (4-1).

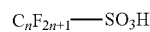

General formula (2-1)

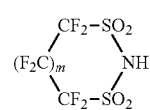

General formula (3-1)

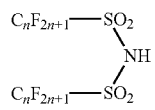

General formula (4-1)

In the general formula (2-1), n is an integer of 0 to 20. In the general formula (3-1), m is an integer of 0 to 2. In the general formula (4-1), n is an integer of 0 to 10.

n in the general formula (2-1) is preferably an integer of 1 to 10.

m in the general formula (3-1) is preferably an integer of 1 or 2.

n in the general formula (4-1) is preferably an integer of 0 to 6.

The ionic liquid may be used alone as the lubricant, or the ionic liquid may be used in combination with a conventional lubricant. Examples of the conventional lubricant include long-chain carboxylic acid, long-chain carboxylic acid ester, perfluoroalkyl carboxylic acid ester, perfluoroalkyl carboxylate, perfluoroalkyl perfluoroalkylcarboxylate, and a perfluoropolyether derivative.

Moreover, an extreme pressure agent may be used in combination at a blending ratio of about 30:70 to 70:30 in a mass ratio in order to maintain a lubricating effect under severe conditions. The extreme pressure agent reacts with a surface of a metal with friction heat generated when the lubricant is partially in contact with the metal in a boundary lubrication region, and forms a coating film of a reaction product. As a result, friction and abrasion are prevented. As the extreme pressure agent, for example, any of a phosphorus-based extreme pressure agent, a sulfur-based extreme pressure agent, a halogen-based extreme pressure agent, an organic metal-based extreme pressure agent, or a complex extreme pressure agent can be used.

Moreover, an anti-rust agent may be optionally used in combination. The anti-rust agent may be any anti-rust agent typically used for this kind of magnetic recording media. Examples of the anti-rust agent include phenols, naphthols, quinones, heterocyclic compounds containing a nitrogen atom, heterocyclic compounds containing an oxygen atom, and heterocyclic compounds containing a sulfur atom. Moreover, the anti-rust agent may be mixed with the lubricant. Alternatively, the anti-rust agent and the lubricant may be deposited as two or more layers by forming a magnetic layer on a non-magnetic support, and applying an anti-rust agent layer on the upper part of the magnetic layer, followed by applying a lubricant layer.

As a solvent of the lubricant, for example, a single use or a combination of alcoholic solvents, such as isopropyl alcohol (IPA), and ethanol, can be used. For example, a mixture of a hydrocarbon-based solvent, such as normal-hexane, and a fluorine-based solvent can be used.

(Magnetic Recording Medium)

A magnetic recording medium of the present invention includes a non-magnetic support, a magnetic layer, and the lubricant of the present invention, and may further include other members according to the necessity.

The magnetic layer is formed on the non-magnetic support.

The lubricant is formed on the magnetic layer.

The lubricant can be applied for so-called a thin film-metal-type magnetic recording medium, in which a magnetic layer formed on a non-magnetic support by a method, such as vapor deposition and sputtering. Moreover, the lubricant can be also applied for a magnetic recording medium having a structure, in which a base layer is disposed between a non-magnetic support and a magnetic layer. Examples of such a magnetic recording medium include a magnetic disk, and a magnetic tape.

FIG. 1 is a cross-sectional view illustrating one example of a hard disk. The hard disk has a structure, in which a substrate 11, a base layer 12, a magnetic layer 13, a protective carbon layer 14, and a lubricant layer 15 are sequentially laminated.

Figure 2:
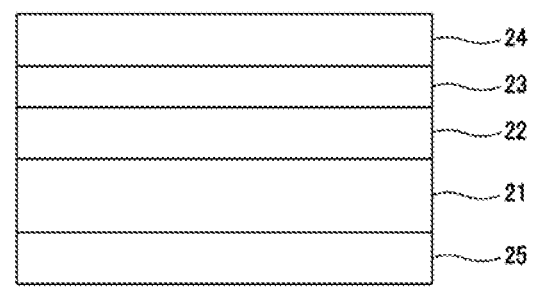
FIG. 2 is a cross-sectional view illustrating one example of a magnetic tape according one embodiment of the present invention.
Figure 3:
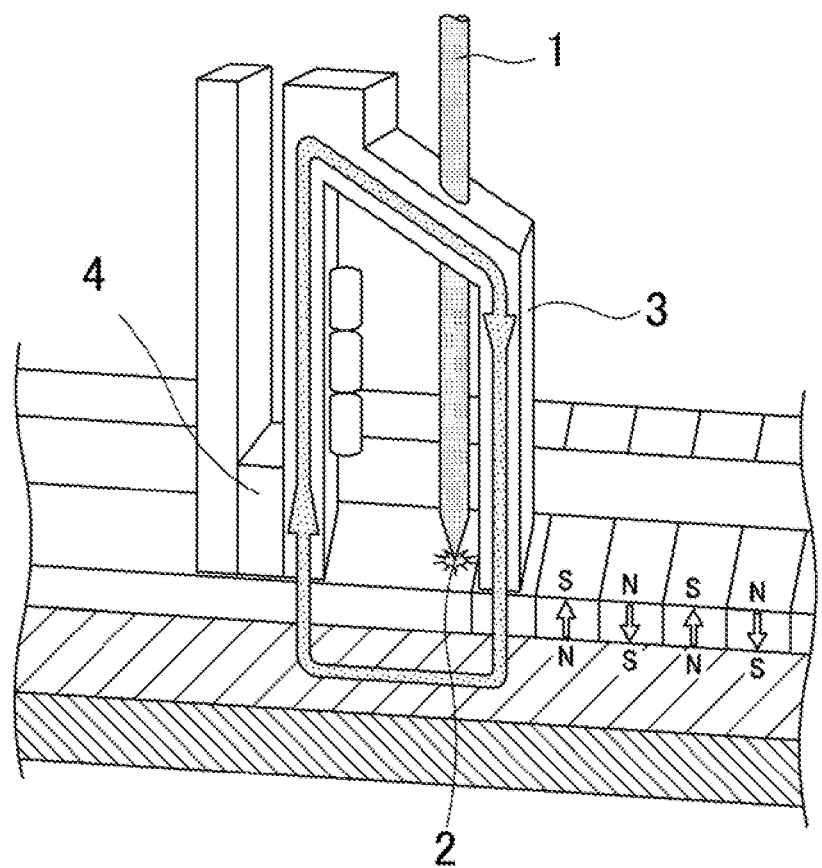
FIG. 3 is a schematic view illustrating heat-assisted magnetic recording.

Moreover, FIG. 2 is a cross-sectional view illustrating one example of a magnetic tape. The magnetic tape has a structure, in which a back-coating layer 25, a substrate 21, a magnetic layer 22, a protective carbon layer 23, and a lubricant layer 24 are sequentially laminated.

In the magnetic disk illustrated in FIG. 1, each of the substrate 11 and the base layer 12 corresponds to the non-magnetic support. In the magnetic tape illustrated in FIG. 2, the substrate 21 corresponds to the non-magnetic support. In the case where a rigid substrate, such as an Al alloy plate, and a glass plate, is used as the non-magnetic support, a surface of the substrate may be made hard by forming an oxidized film, such as anodizing or a Ni—P coating on the surface of the substrate.

Each of the magnetic layers 13 and 22 is formed as a continuous film by a method, such as plating, sputtering, vacuum deposition, and plasma CVD. Examples of the magnetic layers 13 and 22 include: longitudinal magnetic recording metal magnetic films formed of metals (e.g., Fe, Co, and Ni), Co—Ni-based alloys, Co—Pt-based alloys, Co—Ni—Pt-based alloys, Fe—Co-based alloys, Fe—Ni-based alloys, Fe—Co—Ni-based alloys, Fe—Ni—B-based alloys, Fe—Co—B-based alloys, or Fe—Co—Ni—B-based alloys; and perpendicular magnetic recording metal magnetic thin films, such as Co—Cr-based alloy thin films, and Co—O-based thin films.

In the case where a longitudinal magnetic recording metal magnetic thin film is formed, particularly, a non-magnetic material, such as Bi, Sb, Pb, Sn, Ga, In, Ge, Si, and Tl, is formed as a base layer 12 on a non-magnetic support in advance, and a metal magnetic material is deposited through vapor deposition or sputtering in a perpendicular direction to diffuse the non-magnetic material into the magnetic metal thin film, to thereby improve a coercive force as well as eliminating orientation to assure in-plane isotropy.

Moreover, a hard protective layer 14 or 23, such as a carbon film, a diamond-formed carbon film, a chromium oxide film, and $SiO_2$ film, may be formed on a surface of the magnetic layer 13 or 22.

Examples of a method for applying the above-mentioned lubricant to such a metal thin film magnetic recording medium include a method for top-coating a surface of the magnetic layer 13 or 22, or a surface of the protective layer 14 or 23 with the lubricant, as illustrated in FIGS. 1 and 2. A coating amount of the lubricant is preferably from 0.1 $mg/m^2$ to 100 $mg/m^2$, and more preferably from 0.2 $mg/m^2$ to 3 $mg/m^2$.

As illustrated in FIG. 2, moreover, a metal thin film magnetic tape may optionally have a back-coating layer 25, other than a metal magnetic thin film, which is the magnetic layer 22.

The back-coating layer 25 is formed by adding a carbon-based powder for imparting conductivity, or an inorganic pigment for controlling a surface roughness to a resin binder, and applying the resin binder mixture. In the present embodiment, the above-described lubricant may be internally added to the back-coating layer 25, or applied to the back-coating layer 25 as top coating. Moreover, the above-described lubricant may be internally added to both the magnetic layer 22 and the back-coating layer 25, or applied to both the magnetic layer 22 and the back-coating layer 25 as top coating.

As another embodiment, moreover, the lubricant can be applied for a so-called coating-type magnetic recording medium, in which a magnetic coating film is formed as a magnetic layer by applying a magnetic coating material onto a surface of a non-magnetic support. In the coating-type magnetic recording medium, the non-magnetic support, a magnetic powder constituting the magnetic coating film, and the resin binder for use can be selected from any of those known in the art.

Examples of the non-magnetic support include: polymer substrates formed of polymer materials, such as polyesters, polyolefins, cellulose derivatives, vinyl-based resins, polyimides, polyamides, and polycarbonate; metal substrates formed of aluminium alloys, or titanium alloys; ceramic substrates formed of alumina glass; and glass substrates. Moreover, a shape of the non-magnetic support is not particularly limited and may be any form, such as a tape, a sheet, and a drum. Furthermore, the non-magnetic support may be subjected to a surface treatment to form fine irregularities in order to control surface properties of the non-magnetic support.

Examples of the magnetic powder include: ferromagnetic iron oxide-based particles, such as $\gamma\text{-Fe}_2\text{O}_3$, cobalt-coated $\gamma\text{-Fe}_2\text{O}_3$; ferromagnetic chromium dioxide; ferromagnetic metal-based particles formed of a metal, such as Fe, Co, and Ni, or an alloy containing any of the above-listed metals; and hexagonal ferrite particles in the form of hexagonal plates.

Examples of the resin binder include: polymers, such as vinyl chloride, vinyl acetate, vinyl alcohol, vinylidene chloride, acrylic acid ester, methacrylic acid ester, styrene, butadiene, and acrylonitrile; copolymers combining two or more selected from the above-listed polymers; polyurethane resins; polyester resins; and epoxy resins. In order to improve dispersibility of the magnetic powder, a hydrophilic polar group, such as a carboxylic acid group, a carboxyl group, and a phosphoric acid group, may be introduced into any of the above-listed binders.

Other than the magnetic powder and the resin binder, additives, such as a dispersing agent, an abrasive, an anti-static agent, and an anti-rust agent, may be added to the magnetic coating film.

As a method for retaining the above-described lubricant in the coating-type magnetic recording medium, there are a method where the lubricant is internally added to the magnetic layer constituting the magnetic coating film formed on the non-magnetic support, a method where the lubricant is applied on a surface of the magnetic layer as top coating, and a combination of the above-listed methods. In the case where the lubricant is internally added into the magnetic coating film, the lubricant is added in an amount of from 0.2 parts by mass to 20 parts by mass relative to 100 parts by mass of the resin binder.

In the case where a surface of the magnetic layer is top-coated with the lubricant, moreover, a coating amount of the lubricant is preferably from 0.1 mg/m$^2$ to 100 mg/m$^2$, and more preferably from 0.2 mg/m$^2$ to 3 mg/m$^2$. As a deposition method in the case where the lubricant is applied as top coating, the ionic liquid is dissolved in a solvent, and the obtained solution may be applied or sprayed, or a magnetic recording medium may be clipped in the solution.

Since the lubricant of the present invention is used, in the present embodiment, an excellent lubricating effect is exhibited to reduce a coefficient of friction, and high thermal stability can be achieved. Moreover, the lubricating effect is not impaired even under severe conditions, such as high temperatures, low temperatures, high humidity, and low humidity.

Accordingly, the magnetic recording medium, to which the lubricant of the present embodiment is applied, exhibits excellent running performances, abrasion resistance, and durability because of a lubricating effect, and can further improve thermal stability.

EXAMPLES

Specific examples of the present invention are explained below. In the examples, ionic liquids were synthesized, and lubricants including the ionic liquids were produced. Then, magnetic disks and magnetic tapes were produced using the lubricants and durability of each disk and durability of each tape were evaluated. Production of a magnetic disk, a durability test of the disk, production of a magnetic tape, and a durability test of the tape were performed in the following manner. Note that, the present invention is not limited to these examples.

<Production of Magnetic Disk>

A magnetic thin film was formed on a glass substrate to produce a magnetic disk as illustrated in FIG. 1, for example, according to International Patent Publication No. WO2005/068589. Specifically, a chemically reinforced glass disk, which was formed of aluminium silicate glass and had an outer diameter of 65 mm, an inner diameter of 20 mm, and a disk thickness of 0.635 mm, was prepared, and a surface of the glass disk was polished so that Rmax of the surface was to be 4.8 nm, and Ra of the surface was to be 0.43 nm. The glass substrate was subjected to ultrasonic cleaning for 5 minutes each in pure water and in isopropyl alcohol (IPA) having the purity of 99.9% or greater, and the washed glass substrate was left to stand in saturated IPA steam for 1.5 minutes, followed by drying. The resultant glass substrate was provided as a substrate 11.

On the substrate 11, a NiAl alloy (Ni: 50 mol %, Al: 50 mol %) thin film in the thickness of 30 nm as a seed layer, a CrMo alloy (Cr: 80 mol %, Mo: 20 mol %) thin film in the thickness of 8 nm as a base layer 12, and a CoCrPtB alloy (Co: 62 mol %, Cr: 20 mol %, Pt: 12 mol %, B: 6 mol %) thin film in the thickness of 15 nm as a magnetic layer 13 were sequentially formed by DC magnetron sputtering.

Subsequently, a 5 nm-thick protective carbon layer 14 formed of amorphous diamond-like carbon was formed by plasma CVD, and the resultant disk sample was subjected to ultrasonic cleaning for 10 minutes in isopropyl alcohol (IPA) having the purity of 99.9% or greater inside a cleaner to remove impurities on a surface of the disk, followed by drying. Thereafter, an IPA solution of an ionic liquid was applied on a surface of the disk by dip coating in the environment of 25° C. and 50% in relative humidity (RH), to form about 1 nm of a lubricant layer 15.

<Disk Durability Test>

A CSS durability test was performed by means of a commercially available strain-gauge-type disk friction-abrasion tester in the following manner. A hard disk was mounted on a rotatable spindle with tightening torque of 14.7 Ncm. Thereafter, a head slider was attached on the hard disk in a manner that a center of an air bearing surface at the inner circumference side of the head slider relative to the hard disk was 17.5 mm from a center of the hard disk. The head used for the measurement was an IBM3370-type inline head, a material of the slider was $Al_2O_3$—TiC, and the head load was 63.7 mN. In the test, the maximum value of friction force was monitored per CSS (contact, start, and stop) in the environment of 100 in cleanliness, 25° C., and 60% RH. The number of times when a coefficient of friction was greater than 1.0 was determined as a result of the CSS durability test. When a result of the CSS durability test was greater than 50,000, the result was represented as ">50,000." Moreover, a CSS durability test was similarly performed after performing a heating test for 3 minutes at a temperature of 300° C., in order to study heat resistance.

<Production of Magnetic Tape>

A magnetic tape having a cross-sectional structure as illustrated in FIG. 2 was produced. First, Co was deposited on a substrate 21 formed of a 5 μm-thick MICTRON (aromatic polyamide) film available from TORAY INDUSTRIES, INC. by oblique deposition to form a magnetic layer 22 formed of a ferromagnetic metal thin film having a film thickness 100 nm. Next, a protective layer 23 formed of a 10 nm-thick diamond-like carbon was formed on a surface of the ferromagnetic metal thin film by plasma CVD, followed by cutting the resultant into a strip having a width of 6 mm. An ionic liquid dissolved in IPA was applied onto the magnetic layer 22 in a manner that a film thickness of the ionic liquid solution was about 1 nm. In this manner, a lubricant layer 24 is formed on the magnetic layer to thereby produce a sample tape.

<Tape Durability Test>

Each sample tape was subjected to a measurement of still durability in an environment having a temperature of −5° C. and in an environment having a temperature of 40° C. and 30% RH, and measurements of a coefficient of friction and shuttle durability in an environment having a temperature of −5° C. and in an environment having a temperature of 40° C. and 90% RH. The still durability was evaluated by a decay time of an output in a paused state decayed by −3 dB. The shuttle resistant was evaluated by the number of shuttles taken until an output was reduced by 3 dB when repeated shuttle run was performed for 2 minutes per time. Moreover, a durability test was similarly performed after performing a heating test for 10 minutes at a temperature of 100° C., in order to study heat resistance.

<FTIR>

The measurement of FTIR was performed by means of FT/IR-460 available from JASCO Corporation according to a transmission method using KBr plates or KBr pellets. The resolution of the measurement was 4 cm$^{-1}$.

<TG/DTA>

In the TG/DTA measurement, the measurement was performed by means of EXSTAR6000 available from Seiko Instruments Inc. at a temperature range of from 30° C. to 600° C. at a heating rate of 10° C./min with introducing air at a flow rate of 200 mL/min.

<NMR>

The $^1$H-NMR spectrum was measured by means of Varian Mercury Plus 300 nuclear magnetic resonance spectrometer (available from Varian, Inc.). A chemical shift of $^1$H-NMR was represented with ppm comparing with an internal standard (CDCl$_3$ at 7.24 ppm). Splitting patterns were presented by denoting a singlet as s, a doublet as d, a triplet as t, a quartet as q, a multiplet as m, and a broad peak as br.

The $^{13}$C-NMR spectrum was measured by means of Varian Gemini-300 (125 MHz) nuclear magnetic resonance spectrometer (available from Varian, Inc.), and a chemical shift of $^{13}$C-NMR was represented with ppm comparing with an internal standard (CDCl$_3$ at 77.0 ppm).

Example 1

Synthesis of nonafluorobutanesulfonic acid-1-octadecylimidazole salt

Nonafluorobutanesulfonic acid-1-octadecylimidazole salt was synthesized according to the following scheme.

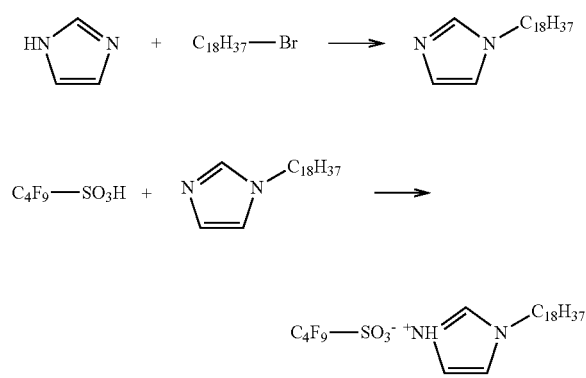

1-Octadecylimidazole was synthesized by the following method.

3 g of imidazole was dissolved in 100 mL of acetonitrile, and 14.9 g of octadecy bromide and 2.51 g potassium hydroxide were added to the resultant solution. The resultant mixture was refluxed for 4 hours under stirring and heating. The solvent was removed. Then, the resultant mixture was extracted with dichloromethane and purified through column chromatography. The obtained product was analyzed through gas chromatography and was found to have a purity of 98.5% or higher.

Subsequently, 3.27 g of the synthesized 1-octadecylimidazole was dissolved in 50 mL of ethanol. To the resultant solution, 3.05 g of nonafluorobutanesulfonic acid was gradually added dropwise. After completion of the dropwise addition, the mixture was stirred for 30 minutes and then refluxed under heating for 1 hour. The solvent was removed. Then, the resultant was recrystallized with a solvent mixture of ethanol/n-hexane to obtain colorless nonafluorobutanesulfonic acid-1-octadecylimidazole salt. The yield was 95%.

The assignment of the FTIR spectrum of the product is depicted below.

The symmetric stretching vibrations of SO$_2$ were observed at 1,134 cm$^{-1}$, asymmetric stretching vibrations of SO$_2$ bonds were observed at 1,355 cm$^{-1}$, symmetric stretching vibrations of CF were observed at 1,246 cm$^{-1}$, symmetric stretching vibrations of a C=N bond were observed at 1,470 cm$^{-1}$, symmetric stretching vibrations of CH$_2$ were observed at 2,852 cm$^{-1}$, asymmetric stretching vibrations of CH$_2$ were observed at 2,920 cm$^{-1}$, and stretching vibrations of a NH bond were observed at 3,158 cm$^{-1}$.

Moreover, peaks of the protons ($^1$H)NMR and carbons ($^{13}$C)NMR of the product in deuterated chloroform are presented below.

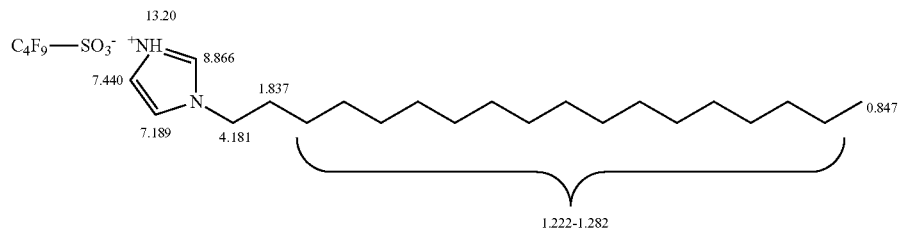

| TABLE 2 | |
|---|---|
| Chemical shift/ppm | CDCl$_3$ |
| 13.20 | 1H, br s |
| 8.866 | 1H, d/2.4 Hz |
| 7.440 | 1H, dd/2.4, 5.0 Hz |
| 7.189 | 1H, dd/2.4, 5.0 Hz |
| 4.181 | 2H, t/9.6 Hz |
| 1.837 | 2H, m |
| 1.222-1.282 | 30H, m |
| 0.847 | 3H, t/9.6 Hz |

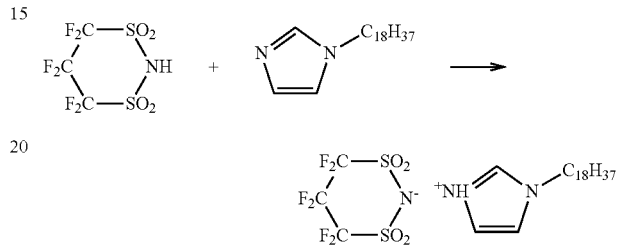

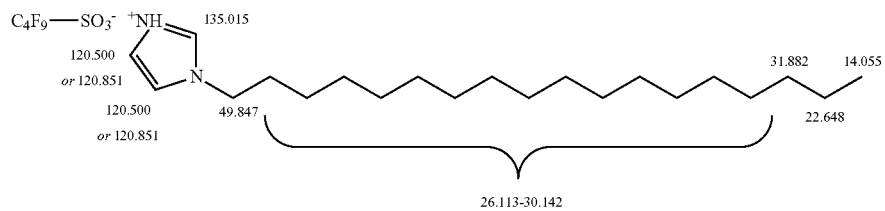

It could be confirmed from the above that nonafluorobutanesulfonic acid-1-octadecylimidazole salt was synthesized.

Figure 4:
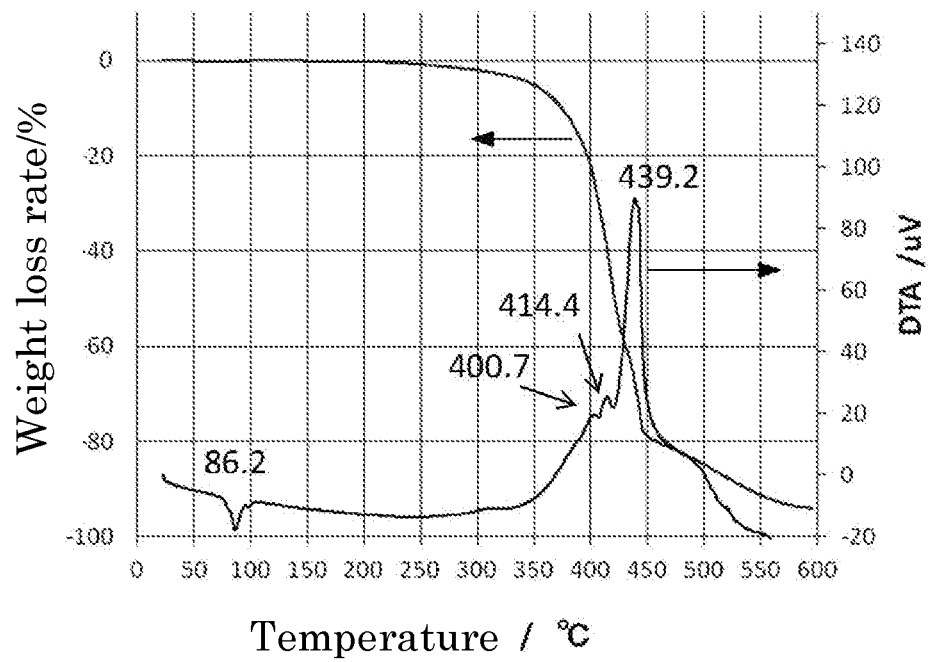
FIG. 4 is the TG/DTA measurement result of the product of Example 1.

The TG/DTA measurement was performed. The TG/DTA measurement result is presented in FIG. 4. The main exothermic peak temperature due to the weight loss was extremely high, i.e., 439.2° C. Moreover, it was suggested that it was a decomposition reaction of the compound because the weight loss was exothermic. The exothermic temperature was improved by 50° C. or more compared to a perfluorooctanesulfonic acid octadecyl ammonium salt. Also, 5% weight loss temperature, 10% weight loss temperature, and 20% weight loss temperature were improved by about 20° C. to about 40° C.

Example 2

Synthesis of hexafluorocyclopropanesulfonimide-1-octadecylimidazole salt

Hexafluorocyclopropanesulfonimide-1-octadecylimidazole salt was synthesized according to the following scheme.

3.2 g of the 1-octadecylimidazole synthesized in Example 1 was dissolved in ethanol. To the resultant solution, a solution prepared by dissolving 2.93 g of hexafluorocyclopropanesulfonimide in ethanol was gradually added dropwise. After completion of the dropwise addition, the mixture was stirred for 30 minutes and then refluxed under heating for 1 hour. The solvent was removed. Then, the resultant was recrystallized with a solvent mixture of ethanol/n-hexane to obtain 5.83 g of colorless hexafluorocyclopropanesulfonimide-1-octadecylimidazole salt. The yield was 95%.

The assignment of the FTIR spectrum of the product is depicted below.

The symmetric stretching vibrations of SO$_2$ were observed at 1,098 cm$^{-1}$, symmetric stretching vibrations of CF$_2$ were observed at 1,175 cm$^{-1}$ and 1,223 cm$^{-1}$, asymmetric stretching vibrations of SO$_2$ bonds were observed at 1,351 cm$^{-1}$, symmetric stretching vibrations of a C=N bond were observed at 1,471 cm$^{-1}$, symmetric stretching vibrations of CH$_2$ were observed at 2,850 cm$^{-1}$, asymmetric stretching vibrations of CH$_2$ were observed at 2,917 cm$^{-1}$, and stretching vibrations of a NH bond were observed at 3,154 cm$^{-1}$ and 3,319 cm$^{-1}$.

Moreover, peaks of the protons ($^1$H)NMR and carbons ($^{13}$C)NMR of the product in deuterated chloroform are presented below.

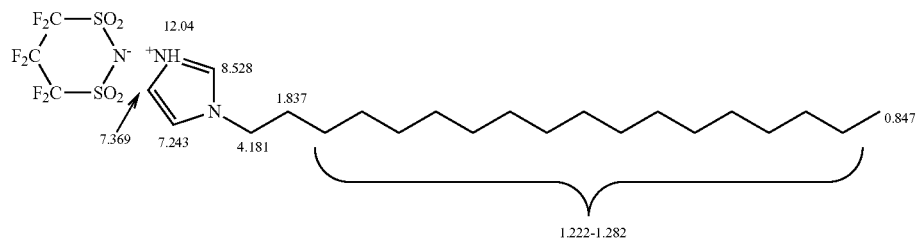

TABLE 3

| Chemical shift/ppm | CDCl$_3$ |
|---|---|
| 12.04 | 1H, br s |
| 8.528 | 1H, d/2.4 Hz |
| 7.369 | 1H, m |
| 7.243 | 1H, t/2.4 Hz |
| 5.03 (unknown) | |
| 4.160 | 2H, t/9.6 Hz |
| 1.855 | 2H, m |
| 1.226-1.299 | 30H, m |
| 0.851 | 3H, t/9.6 Hz |

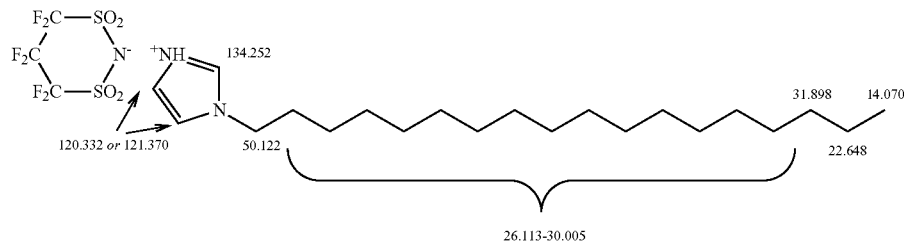

It could be confirmed from the above that hexafluorocyclopropanesulfonimide-1-octadecylimidazole salt was synthesized.

Figure 5:
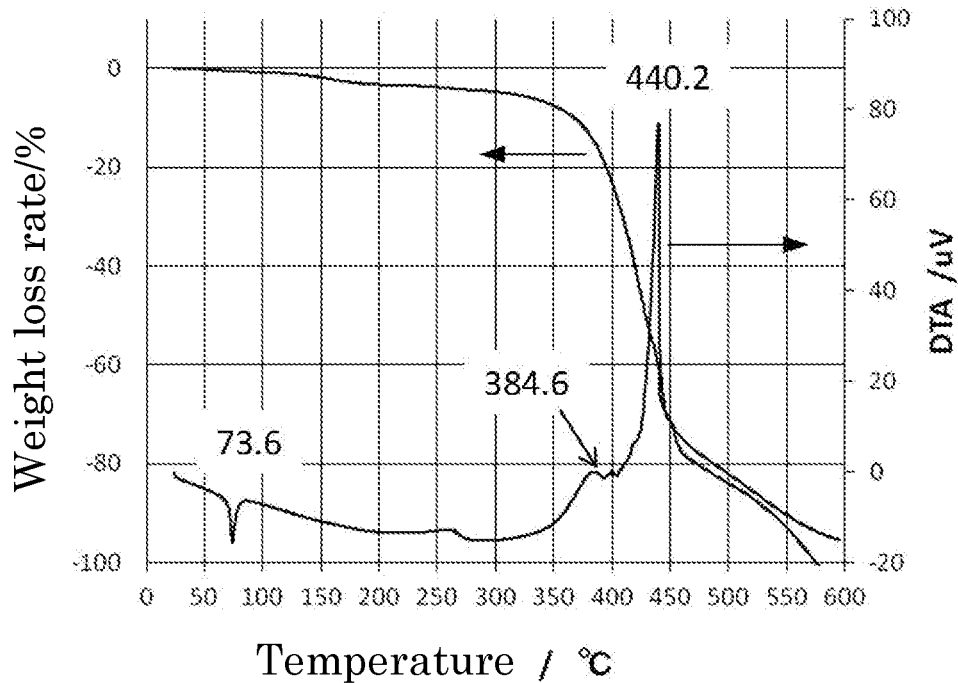
FIG. 5 is the TG/DTA measurement result of the product of Example 2.

The TG/DTA measurement was performed. The TG/DTA measurement result is presented in FIG. 5. The main exothermic peak temperature due to the weight loss was extremely high, i.e., 440.2° C. Moreover, it was suggested that it was a decomposition reaction of the compound because the weight loss was exothermic. The exothermic temperature was improved by about 54° C. compared to a perfluorooctanesulfonic acid octadecyl ammonium salt. Also, 5% weight loss temperature, 10% weight loss temperature, and 20% weight loss temperature were improved by about 20° C. to about 40° C. Moreover, its thermal stability was much higher than those of Z-DOL and Z-Tetraol used in magnetic recording media.

The synthesized ionic liquids are collectively presented in the following Table 4.

The ionic liquids synthesized in Examples 1 and 2 are referred to as Ionic Liquids 1 and 2. The exothermic peak temperatures, 5% weight loss temperatures, 10% weight loss temperatures, and 20% weight loss temperatures are also presented.

Comparative Example 1 was a perfluorooctanesulfonic acid octadecyl ammonium salt ($C_8F_{17}SO_3^-H_3N^+C_{18}H_{37}$). The perfluorooctanesulfonic acid octadecyl ammonium salt was synthesized with reference to non-patent literature (Novel ionic liquid lubricants for magnetic thin film media, Hirofumi Kondo et al., IEEE Trans. Magn., 2013, Vol. 49, issue 7, pp. 3756-3759).

Comparative Example 2 was Fomblin Z-DOL.

Comparative Example 3 was Z-Tetraol (ZTMD).

TABLE 4

| Names | Compounds | 5% weight loss temperature/° C. | 10% weight loss temperature/° C. | 20% weight loss temperature/° C. | Exothermic peak temperature/° C. |
|---|---|---|---|---|---|
| Ionic Liquid 1 (Example 1) | Nonafluorobutane-sulfonic acid-1-octadecyl-imidazole salt | 349.27 | 374.97 | 397.51 | 439.2 |
| Ionic Liquid 2 (Example 2) | Hexafluorocyclo-propanesulfonimide-1-octadecyl-imidazole salt | 309.35 | 367.69 | 395.38 | 440.2 |

TABLE 4-continued

| Names | Compounds | 5% weight loss temperature/° C. | 10% weight loss temperature/° C. | 20% weight loss temperature/° C. | Exothermic peak temperature/° C. |
|---|---|---|---|---|---|
| Comparative Ionic Liquid 1 (Comparative Example 1) | Perfluorooctane-sulfonic acid octadecyl ammonium salt | 328 | 343.4 | 358.4 | 386.3 |
| Comparative Lubricant 1 (Comparative Example 2) | Z-DOL | 178 | 197 | 226 | 354.6 |
| Comparative Lubricant 12 (Comparative Example 3) | Z-Tetraol | 243 | 261 | 282 | — |

Next, durability was studied by using a lubricant using the ionic liquid for a magnetic recording medium.

Example 3

The above-described magnetic disk was produced using a lubricant including nonafluorobutanesulfonic acid-1-octadecylimidazole salt, which is a protic ionic liquid in Example 1. As presented in Table 5, the CSS measurement of the magnetic disk was greater than 50,000 times, and the CSS measurement of the magnetic disk after the heating test was also greater than 50,000 times. Therefore, the magnetic disk exhibited excellent durability.

Example 4

The above-described magnetic disk was produced using a lubricant including hexafluorocyclopropanesulfonimide-1-octadecylimidazole salt, which is a protic ionic liquid in Example 2. As presented in Table 5, the CSS measurement of the magnetic disk was greater than 50,000 times, and the CSS measurement of the magnetic disk after the heating test was also greater than 50,000 times. Therefore, the magnetic disk exhibited excellent durability.

Comparative Example 4

The above-described magnetic disk was produced using a lubricant including perfluorooctane sulfonic acid octadecyl ammonium salt ($C_8F_{17}SO_3^-H_3N^+C_{18}H_{37}$) of [Comparative Example 1] presented in Table 4. As presented in Table 5, the durability of the magnetic disc measured by the CSS was greater than 50,000 times, and even after the heating test, was also greater than 50,000 times. There was no significant difference in properties of the disk compared to Examples.

Comparative Example 5

The above-described magnetic disk was produced using a lubricant including Z-DOL of [Comparative Example 2] presented in Table 4. As presented in Table 5, the durability of the magnetic disk measured by the CSS measurement was greater than 50,000 times, but after the heating test, the CSS durability started to deteriorate at 12,000 times. Compared to Examples, the magnetic disk lacked thermal resistance, and therefore it was considered that the durability was deteriorated after the heating.

Comparative Example 6

The above-described magnetic disk was produced using a lubricant including Z-Tetraol of [Comparative Example 3] presented in Table 4. As presented in Table 5, the durability of the magnetic disk measured by the CSS measurement was greater than 50,000 times, but after the heating test, the CSS durability started to deteriorate at 36,000 times. Regarding the thermal resistance, the durability was improved compared with Z-DOL, but the magnetic disk lacked thermal resistance compared to Examples. It was therefore considered that the durability was deteriorated after the heating.

TABLE 5

|  | CSS durability | | CSS durability after heating | |
|---|---|---|---|---|
| Ex. 3 | 25° C., 60% RH | >50,000 | 25° C., 60% RH | >50,000 |
| Ex. 4 | 25° C., 60% RH | >50,000 | 25° C., 60% RH | >50,000 |
| Comp. Ex. 4 | 25° C., 60% RH | >50,000 | 25° C., 60% RH | >50,000 |
| Comp. Ex. 5 | 25° C., 60% RH | >50,000 | 25° C., 60% RH | 12,000 |
| Comp. Ex. 6 | 25° C., 60% RH | >50,000 | 25° C., 60% RH | 36,000 |

As is clear from the descriptions above, the lubricant of the present invention including the ionic liquid of the present invention could maintain excellent lubricity even under the high temperature storage conditions, and moreover could maintain the CSS lubricity over a long period.

Next, examples where Ionic Liquids 1 and 2, Comparative Ionic Liquid 1, and Comparative Lubricants 1 and 2 were applied for magnetic tapes are described.

Example 5

The above-described magnetic tape was produced using a lubricant including Ionic Liquid 1. As presented in Table 6, a coefficient of friction of the magnetic tape after 100 times of the shuttle running was 0.20 in the environment having a temperature of −5° C., and 0.22 in the environment having a temperature of 40° C. and relative humidity of 90%. Moreover, the still durability test was greater than 60 min in the environment having a temperature of −5° C., and greater than 60 min in the environment having a temperature of 40° C. and relative humidity of 30%. Moreover, the shuttle durability test was greater than 200 times in the environment having a temperature of −5° C., and greater than 200 times in the environment having a temperature of 40° C. and relative humidity of 90%. Moreover, a coefficient of friction of the magnetic tape after 100 times of the shuttle running after the heating test was 0.20 in the environment having a temperature of −5° C., and 0.23 in the environment having a temperature of 40° C. and relative humidity of 90%. Also, the still durability test after the heating test was greater than 60 min in the environment having a temperature of −5° C., and greater than 60 min in the environment having a temperature of 40° C. and relative humidity of 30%. Moreover, the shuttle durability test after the heating test was greater than 200 times in the environment having a temperature of −5° C., and greater than 200 times in the environment having a temperature of 40° C. and relative humidity of 90%. It was found from the results above that the magnetic tape, to which Ionic Liquid 1 had been applied, had excellent abrasion properties, still durability, and shuttle durability.

Example 6

The above-described magnetic tape was produced using a lubricant including Ionic Liquid 2. As presented in Table 6, a coefficient of friction of the magnetic tape after 100 times of the shuttle running was 0.21 in the environment having a temperature of −5° C., and 0.23 in the environment having a temperature of 40° C. and relative humidity of 90%. Moreover, the still durability test was greater than 60 min in the environment having a temperature of −5° C., and greater than 60 min in the environment having a temperature of 40° C. and relative humidity of 30%. Moreover, the shuttle durability test was greater than 200 times in the environment having a temperature of −5° C., and greater than 200 times in the environment having a temperature of 40° C. and relative humidity of 90%. Moreover, a coefficient of friction of the magnetic tape after 100 times of the shuttle running after the heating test was 0.22 in the environment having a temperature of −5° C., and 0.24 in the environment having a temperature of 40° C. and relative humidity of 90%. The still durability test after the heating test was greater than 60 min in the environment having a temperature of −5° C., and greater than 60 min in the environment having a temperature of 40° C. and relative humidity of 30%. Moreover, the shuttle durability test after the heating test was greater than 200 times in the environment having a temperature of −5° C., and greater than 200 times in the environment having a temperature of 40° C. and relative humidity of 90%. It was found from the results above that the magnetic tape, to which Ionic Liquid 2 had been applied, had excellent abrasion properties, still durability, and shuttle durability.

Comparative Example 7

The above-described magnetic tape was produced using perfluorooctane sulfonic acid octadecyl ammonium salt that was the Comparative Ionic Liquid 1 of Comparative Example 1. As presented in Table 6, a coefficient of friction of the magnetic tape after 100 times of the shuttle running was 0.20 in the environment having a temperature of −5° C., and 0.23 in the environment having a temperature of 40° C. and relative humidity of 90%. Moreover, the still durability test was greater than 60 min in the environment having a temperature of −5° C., and greater than 60 min in the environment having a temperature of 40° C. and relative humidity of 30%. Moreover, the shuttle durability test was greater than 200 times in the environment having a temperature of −5° C., and greater than 200 times in the environment having a temperature of 40° C. and relative humidity of 90%. However, a coefficient of friction of the magnetic tape after 100 times of the shuttle running after the heating test was 0.23 in the environment having a temperature of −5° C., and increased to 0.26 in the environment having a temperature of 40° C. and relative humidity of 90%. The still durability test after the heating test was greater than 60 min in the environment having a temperature of −5° C., and greater than 60 min in the environment having a temperature of 40° C. and relative humidity of 30%. Moreover, the shuttle durability test after the heating test was greater than 200 times in the environment having a temperature of −5° C., and greater than 200 times in the environment having a temperature of 40° C. and relative humidity of 90%. It was found from the results above that the magnetic tape, to which Comparative Ionic Liquid 1 had been applied, had excellent still durability and shuttle durability, but the coefficient of friction increased after the heating test.

Comparative Example 8

The above-described magnetic tape was produced using a lubricant including Z-DOL of Comparative Example 2. As presented in Table 6, a coefficient of friction of the magnetic tape after 100 times of the shuttle running was 0.25 in the environment having a temperature of −5° C., and 0.30 in the environment having a temperature of 40° C. and relative humidity of 90%. Moreover, the still durability test was 12 min in the environment having a temperature of −5° C., and 48 min in the environment having a temperature of 40° C. and relative humidity of 30%. Moreover, the shuttle durability test was 59 times in the environment having a temperature of −5° C., and 124 times in the environment having a temperature of 40° C. and relative humidity of 90%. Moreover, a coefficient of friction of the magnetic tape after 100 times of the shuttle running after the heating test was 0.32 in the environment having a temperature of −5° C., and increased to 0.35 in the environment having a temperature of 40° C. and relative humidity of 90%. The still durability test after the heating test was 12 min in the environment having a temperature of −5° C., and 15 min in the environment having a temperature of 40° C. and relative humidity of 30%. Moreover, the shuttle durability test after the heating test was 46 times in the environment having a temperature of −5° C., and 58 times in the environment having a temperature of 40° C. and relative humidity of 90%. It was found from the results above that the magnetic tape, to which the compound of Comparative Example 2 had been applied, had a high coefficient of friction, and significant deteriorations in still durability and shuttle durability.

Comparative Example 9

The above-described magnetic tape was produced using a lubricant including the compound Z-Tetraol of Comparative Example 3. As presented in Table 6, a coefficient of friction of the magnetic tape after 100 times of the shuttle running was 0.22 in the environment having a temperature of −5° C., and 0.26 in the environment having a temperature of 40° C. and relative humidity of 90%. Moreover, the still durability test was 25 min in the environment having a temperature of −5° C., and 35 min in the environment having a temperature of 40° C. and relative humidity of 30%. Moreover, the shuttle durability test was 65 times in the environment having a temperature of −5° C., and 156 times in the environment having a temperature of 40° C. and relative humidity of 90%. As mentioned, the durability was improved compared to Comparative Example 8 but specifications of magnetic tapes were not satisfied. Moreover, a coefficient of friction of the magnetic tape after 100 times of the shuttle running after the heating test was 0.28 in the environment having a temperature of −5° C., and increased to 0.32 in the environment having a temperature of 40° C. and relative humidity of 90%. The still durability test after the heating test was 23 min in the environment having a temperature of −5° C., and 31 min in the environment having a temperature of 40° C. and relative humidity of 30%. Moreover, the shuttle durability test after the heating test was 55 times in the environment having a temperature of −5° C., and 126 times in the environment having a temperature of 40° C. and relative humidity of 90%. It was found from the results above that the magnetic tape, to which the lubricant Z-Tetraol of Comparative Example 3 had been applied, had a high coefficient of friction, and significant deteriorations in still durability and shuttle durability, compared to Examples.

4 reproducing head (TMR element)

11 substrate 12 base layer 13 magnetic layer 14 protective carbon layer 15 lubricant layer 21 substrate 22 magnetic layer 23 protective carbon layer 24 lubricant layer 25 back-coating layer

The invention claimed is:

1. A lubricant comprising:
   an extreme pressure agent, and
   an ionic liquid, which includes a conjugate acid (B⁺) and a conjugate base (X⁻), and is protic,

TABLE 6

| | Coefficient of friction after 100 running | | Still durability/min | | Shuttle durability/times | | Still durability after heating/min | | Coefficient of friction after 100 running | | Shuttle durability after heating/times | |
|---|---|---|---|---|---|---|---|---|---|---|---|---|
| Ex. 5 | −5° C. | 0.20 | −5° C. | >60 | −5° C. | >200 | −5° C. | 0.20 | −5° C. | >60 | −5° C. | >200 |
| | 40° C., 90% RH | 0.22 | 40° C., 30% RH | >60 | 40° C., 90% RH | >200 | 40° C., 90% RH | 0.23 | 40° C., 30% RH | >60 | 40° C., 90% RH | >200 |
| Ex. 6 | −5° C. | 0.21 | −5° C. | >60 | −5° C. | >200 | −5° C. | 0.22 | −5° C. | >60 | −5° C. | >200 |
| | 40° C., 90% RH | 0.23 | 40° C., 30% RH | >60 | 40° C., 90% RH | >200 | 40° C., 90% RH | 0.24 | 40° C., 30% RH | >60 | 40° C., 90% RH | >200 |
| Comp. Ex. 7 | −5° C. | 0.20 | −5° C. | >60 | −5° C. | >200 | −5° C. | 0.23 | −5° C. | >60 | −5° C. | >200 |
| | 40° C., 90% RH | 0.23 | 40° C., 30% RH | >60 | 40° C., 90% RH | >200 | 40° C., 90% RH | 0.26 | 40° C., 30% RH | >60 | 40° C., 90% RH | >200 |
| Comp. Ex. 8 | −5° C. | 0.25 | −5° C. | 12 | −5° C. | 59 | −5° C. | 0.32 | −5° C. | 12 | −5° C. | 46 |
| | 40° C., 90% RH | 0.30 | 40° C., 30% RH | 48 | 40° C., 90% RH | 124 | 40° C., 90% RH | 0.35 | 40° C., 30% RH | 15 | 40° C., 90% RH | 58 |
| Comp. Ex. 9 | −5° C. | 0.22 | −5° C. | 25 | −5° C. | 65 | −5° C. | 0.28 | −5° C. | 23 | −5° C. | 55 |
| | 40° C., 90% RH | 0.26 | 40° C., 30% RH | 35 | 40° C., 90% RH | 156 | 40° C., 90% RH | 0.32 | 40° C., 30% RH | 31 | 40° C., 90% RH | 126 |

It was also evident from the results above that the magnetic tape, to which the lubricant of the present invention including the ionic liquid of the present invention had been applied, exhibited excellent abrasion resistance, still durability, and shuttle durability. In case of Z-DOL or Z-Tetraol as Comparative Example, however, deterioration in the durability was significant similarly to the case of the above-described disk. In case of the lubricant including perfluorooctane sulfonic octadecyl ammonium salt, moreover, the magnetic tape had excellent durability, but the coefficient of friction slightly increased after the heating.

As is clear from the explanations above, the lubricant including an ionic liquid, which contains a conjugate acid (B⁺) and a conjugate base (X⁻), is represented by the general formula (1), and is protic, can maintain lubricity even under high temperature conditions, and can maintain lubricity over a long period. Accordingly, a magnetic recording medium using the lubricant had extremely excellent running performances, abrasion resistance, and durability.

REFERENCE SIGNS LIST 1 laser light
2 near-field light
3 recording head (PMR element)

wherein the ionic liquid is represented by the following general formula (1):

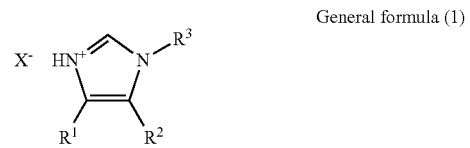

General formula (1)

where R¹ and R² each represent a hydrogen atom or R¹ and R² form a benzene ring together with carbon atoms to which R¹ and R² are bonded, and R³ represents a straight-chain hydrocarbon group having 10 or more carbon atoms in the general formula (1).

2. The lubricant according to claim 1,
wherein the conjugate base is represented by any one of the following general formulae (2) to (4):

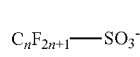

General formula (2)

-continued

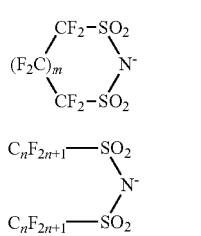
General formula (3)

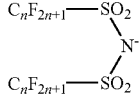
General formula (4)

where n is an integer of 0 to 20 in the general formula (2), m is an integer of 0 to 2 in the general formula (3), and n is an integer of 0 to 10 in the general formula (4).

3. A magnetic recording medium comprising:
a non-magnetic support;
a magnetic layer on the non-magnetic support; and
a lubricant on the magnetic layer,
wherein the lubricant comprises an ionic liquid, which includes a conjugate acid ($B^+$) and a conjugate base ($X^-$), and is protic,
wherein the ionic liquid is represented by the following general formula (1):

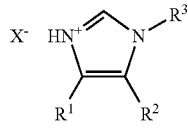
General formula (1)

where $R^1$ and $R^2$ each represent a hydrogen atom or $R^1$ and $R^2$ form a benzene ring together with carbon atoms to which $R^1$ and $R^2$ are bonded, and $R^3$ represents a straight-chain hydrocarbon group having 10 or more carbon atoms in the general formula (1).

4. An ionic liquid comprising:
a conjugate acid ($B^+$); and
a conjugate base ($X^-$),
wherein the ionic liquid is represented by the following general formula (1) and is protic:

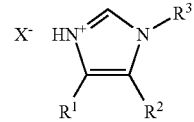
General formula (1)

where $R^1$ and $R^2$ form a benzene ring together with carbon atoms to which $R^1$ and $R^2$ are bonded, and $R^3$ represents a straight-chain hydrocarbon group having 10 or more carbon atoms in the general formula (1).

5. The ionic liquid according to claim 4,
wherein the conjugate base is represented by any one of the following general formulae (2) to (4):

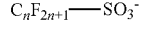
General formula (2)

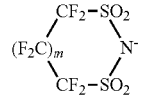
General formula (3)

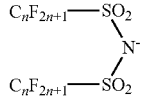
General formula (4)

where n is an integer of 0 to 20 in the general formula (2), m is an integer of 0 to 2 in the general formula (3), and n is an integer of 0 to 10 in the general formula (4).

* * * * *